United States Patent [19]

Toedtli

[11] Patent Number: 5,235,852
[45] Date of Patent: Aug. 17, 1993

[54] METHOD FOR MEASURING YARN STRENGTH

[75] Inventor: Sergej Toedtli, Wollerau, Switzerland

[73] Assignee: Siegfried Peyer AG, Wollerau, Switzerland

[21] Appl. No.: 852,516

[22] Filed: Mar. 17, 1992

Related U.S. Application Data

[63] Continuation-in-part of Ser. No. 499,359, Mar. 7, 1990, abandoned.

[30] Foreign Application Priority Data

Aug. 3, 1988 [CH] Switzerland .................. 2949/88

[51] Int. Cl.⁵ .............................................. G01L 5/10
[52] U.S. Cl. ................................... 73/160; 28/227
[58] Field of Search ............... 73/104, 788, 835, 828, 73/830, 159, 160, 760; 28/219, 226; 83/522.14, 522.26; 356/384, 385; 364/469, 470

[56] References Cited

U.S. PATENT DOCUMENTS

| | | | |
|---|---|---|---|
| 2,340,401 | 2/1944 | Martin | 73/835 |
| 3,319,462 | 5/1967 | Ostrowski | 73/835 |
| 3,554,068 | 1/1971 | Schwartz | 28/227 |
| 3,731,069 | 5/1973 | Goto et al. | 73/160 |
| 3,795,906 | 3/1974 | Erbstein | 73/160 |
| 3,854,356 | 12/1974 | Okreglak | 28/226 |
| 3,892,951 | 7/1975 | Stutz | 73/160 |
| 4,036,445 | 7/1977 | Stutz et al. | 73/160 |
| 4,173,787 | 11/1979 | Katona et al. | 364/550 |
| 4,737,904 | 4/1988 | Ominato | 364/469 |
| 4,817,425 | 4/1989 | Ueda et al. | 73/160 |

FOREIGN PATENT DOCUMENTS

| | | | |
|---|---|---|---|
| 2152295 | 4/1972 | Fed. Rep. of Germany | 28/227 |
| 0699799 | 12/1965 | Italy | 28/227 |

Primary Examiner—William A. Cuchlinski, Jr.
Assistant Examiner—W. Morris Worth
Attorney, Agent, or Firm—Walter C. Farley

[57] ABSTRACT

In method of yarn strength measurement, the yarn of which the strength is being tested is grabbed while the yarn is moving during a production or processing process, in a spinning machine or a yarn-processing machine, a spooling frame or open-end spinning machine, by a clamp and is made to tear. The forces arising during tearing are determined using a test device and utilizing the electronic infrastructure already extant in the yarn cleaner to ascertain the yarn strength.

14 Claims, 4 Drawing Sheets

METHOD FOR MEASURING YARN STRENGTH

CROSS REFERENCE TO RELATED APPLICATION

This is a continuation-in-part of Ser. No. 07/499,359 filed Mar. 7, 1990 and now abandoned.

FIELD OF THE INVENTION

This invention concerns an on-line method of measuring yarn strength.

BACKGROUND OF THE INVENTION

It is very important in the textile industry that yarn strength be determined during a continuous process, i.e., while the yarn is in motion, without causing delays and in a simple manner, so that reliable prediction of the ultimate suitability of the yarn for many applications is possible. The conventional testing procedures for yarn strength are presently less satisfactory because of increasing automation of the textile industry and the ensuing extremely accelerated work rates. Frequently, the yarn-strength test result is available only when the work already has been completed, ruling out anticipatory corrective steps.

Procedures for testing yarn strength are known, for example, from U.S. Pat. No. 4,173,787 and from European patent document A2 0,241,894. They share the drawback that the yarn is tested off-line, that is, outside the continuous yarn processing, and that therefore no correction is possible during the processing. In view of the measurement being by sampling in a laboratory, the data so obtained are subject to doubt.

Another drawback of the known test methods consists in only allowing static yarn tests, which are of subordinate significance to the yarn processor because the yarn is stressed only impulsively, i.e. dynamically in the ensuing stages.

SUMMARY OF THE INVENTION

An object of the invention is particularly to provide a method for continuously measuring yarn strength on line, i.e., without time loss, making possible areal, gapless monitoring of yarn production or processing at minimal checking cost per yarn bobbin. Another object is the creation of apparatus making use of extant electronics in the yarn cleaners of the state of the art to measure yarn strength by the method of the invention.

The above objects are achieved by the invention by means of a method in which apparatus causes yarn to move longitudinally through processing machinery and a clamp engages and holds the yarn, the resulting force on the yarn causing it to tear. A test apparatus measures the force required to tear the yarn and thereby determines yarn strength.

Essentially, the advantages offered by the invention are that by means of the method of the invention gapless, i.e., on-line determination of yarn strength is made possible during a continuous process such as spinning, quilling or twisting. Moreover, employing the electronic infrastructure of an already extant yarn cleaner, simple and economical design can be applied.

BRIEF DESCRIPTION OF THE DRAWINGS

Several illustrative embodiments of the invention simultaneously elucidating the principle of operation are discussed in further detail below and shown in the drawings wherein.

DESCRIPTION OF THE PREFERRED EMBODIMENTS

Figure 1:
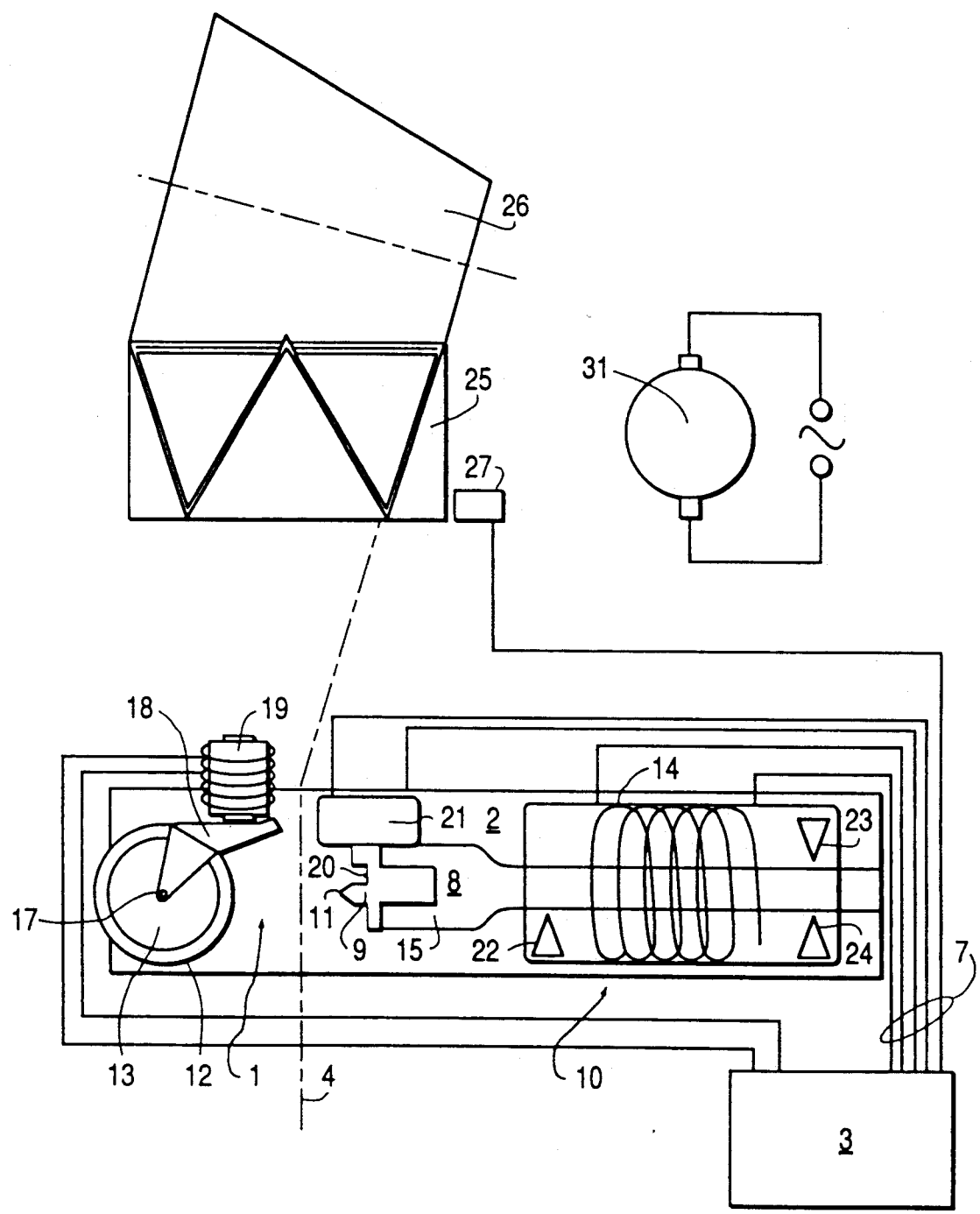
FIG. 1 is a cross-section of the apparatus of the invention with a clamp means open.

FIG. 1 shows the preferred mode of an apparatus with which to implement the method of the invention. Essentially the apparatus of the invention comprises a clamp 1 for the yarn 4, a measuring system 2 to determine the yarn strength and a central processing unit 3 to analyze the obtained test data and, if called for, an optional cutter 8 to sever the yarn 4. The yarn is moved through the system by conventional apparatus such as a motor 3? driving a guide 25 and bobbin 26 which apply a longitudinal force to the yarn 4.

The clamp is integrated into the cutter 8 which includes a guided, longitudinally displaceable knife 9 supported on rest points 22, 23 and 24 and drive means 10 for moving the knife 9 together with its blade 11 so that the blade contacts a drum 13, the outer surface 12 of which serves as an anvil. Drive means 10 essentially comprises a knife-holder 15 mounted in a longitudinally displaceable manner in an electromagnetic coil 14.

Further details concerning the cutter 8 may be found in Swiss patent 478,051.

Figure 1A:
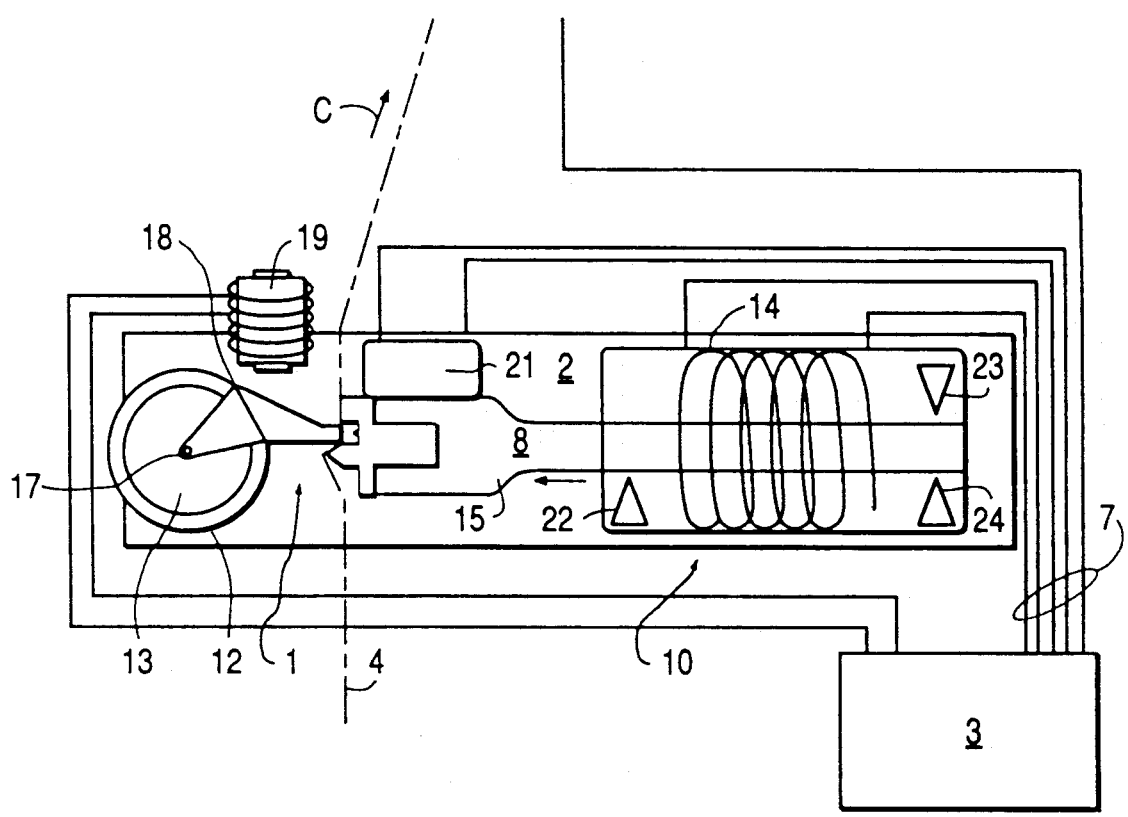
FIG. 1A is a view similar to FIG. 1 with the clamp means open.

The clamp cooperating with cutter 8 essentially includes a flap 18 which is mounted for limited rotational movement about a shaft 17 of drum 13. The flap is held in the open state shown in FIG. 1, which is the rest position, by energization of the electromagnetic solenoid 19. When it is desired to measure the yarn strength, the solenoid 19 is deenergized by the central processing unit 3 and the flap 18 is moved clockwise, either by gravity or by force of a restoring spring, not shown, into a recess 20 of the knife 9 which is concurrently displaced toward the flap, as shown in FIG. 1A. When the end of the flap enters recess 20, the yarn 4 is clamped between the end of flap 18 and the walls of recess 20 and the force exerted by the yarn-moving apparatus restrained by the clamp causes the yarn to tear. The resulting tear force on the clamp is converted by a piezoelectric force pickup 21 cooperating with the rest points 22, 23, 24, into an electrical pulse transmitted through the lines 7 to the central processing unit for analysis.

The yarn 4 may be clamped in the continuously flowing state and then be made to tear. However, the incoming and outgoing yarn 4 also may be clamped and be made to tear, depending on the needs of the yarn processing operator. Lastly, the apparatus of the invention allows clamping and tearing a spliced site of the yarn 4 in order to ascertain the yarn strength at the splice, the weakest spot.

In a special embodiment wherein the apparatus of the invention is integrated into a cross-wound bobbin winder or into an open-end spinning machine, the clamping by means of the clamp i is synchronized with the position of a grooved cylinder 25 or open-end spinning machine driven by the motor 31 by means of the sensor 27 so that clamping takes place only at positions of the grooved cylinder 25 at which the crosswound bobbin 26 shall not be damaged.

Figure 2:
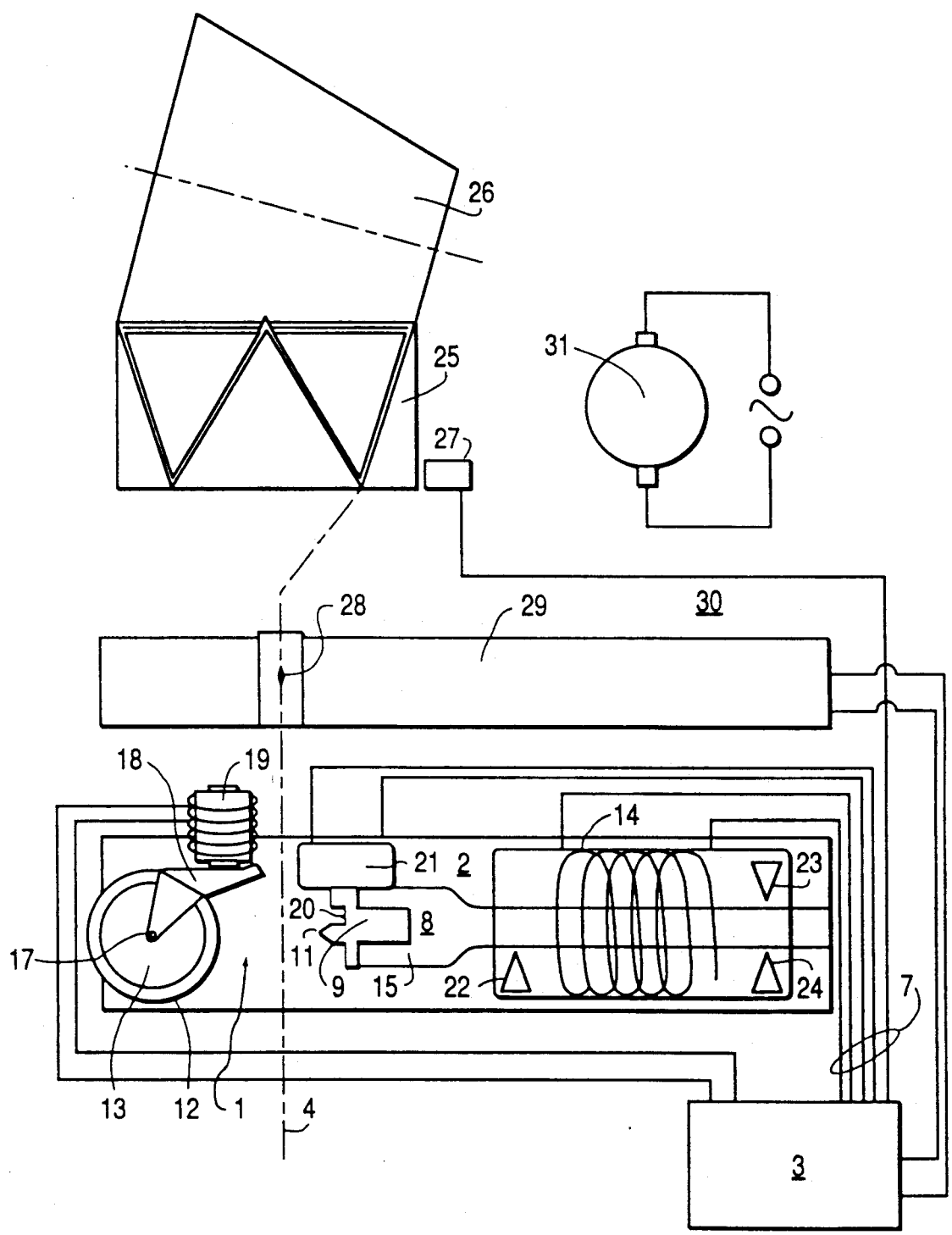
FIG. 2 is a cross-section of the apparatus of the invention wherein the clamp means is combined with a yarn cleaner.

FIG. 2 shows a further embodiment wherein the clamp 1 is combined with a yarn cleaner 30 comprising an optical sensor 29 (which typically includes a light emitting diode illuminating the area subject to measurement and a photodetector, not shown in further detail), conductor means 7 for transmitting for analysis the signals generated by the optical sensor 29, the central processing unit 3 to analyze the electrical signals from the optical sensor 29, and the clamp and cutter 8. Operation is such that when a yarn defect 28 is detected and recognized by the processing unit 3, solenoid 19 is de-energized by the central processing unit, displacing the flap 18 into recess 20 of the knife 10 moving toward flap 18 so that the yarn 4 is clamped in the clearance 20 and thereby is made to tear. The resulting tear force is converted by the piezoelectric force pickup 21 cooperating with the rest points 22, 23, 24 into an electric pulse transmitted through lines 7 to the central processing unit 3 for analysis.

When an impermissible deviation of quality in the yarn 4 is detected in the yarn cleaner 30, the moving yarn 4 preferably is clamped about 1.5 m after the determination of the yarn defect 28 so that the tear-strength shall be ascertained at a good location of the yarn 4.

Figure 3A:
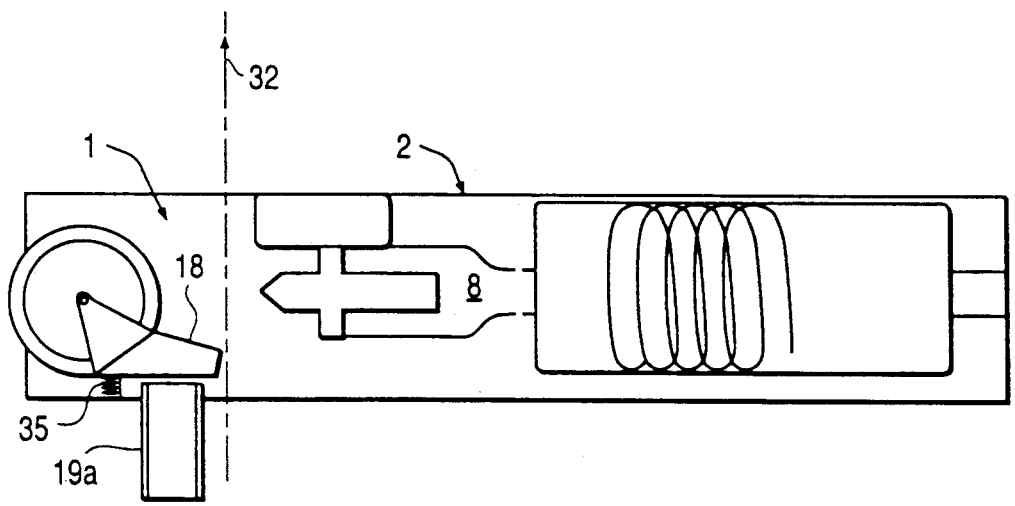
FIGS. 3A and 3B are cross-sectional views of a clamp means of the invention in the open and in the closed states, respectively.
Figure 3B:
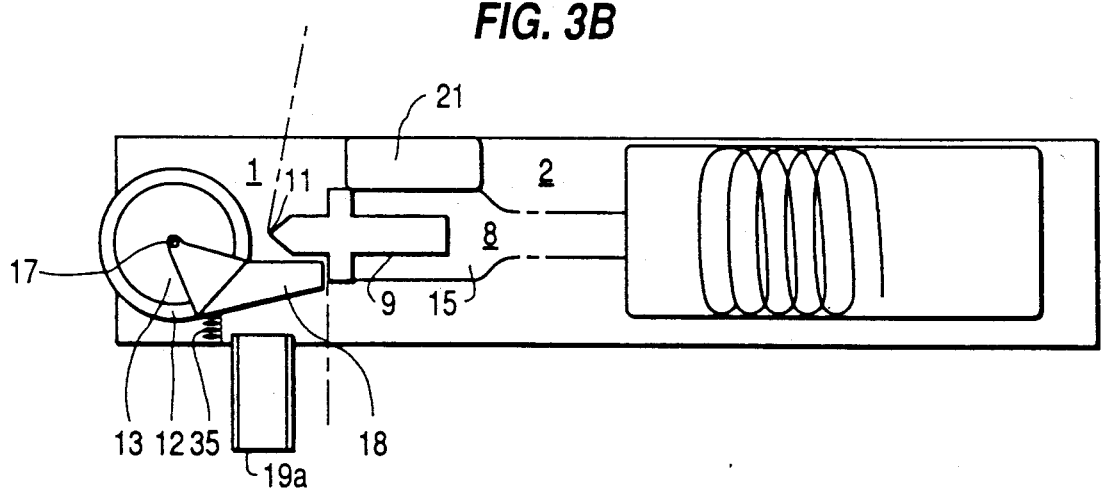

FIG. 3A shows a further embodiment of the clamp 1 of the apparatus of the invention when open and FIG. 3B shows it in the closed state. In this embodiment the flap 18, contrary to the embodiment of FIGS. 1, 1A and 2, is pivoted into the position of FIG. 3A against the force of a spring 35 by means of an energized solenoid 19a located underneath the cutter 8 and the yarn 4 moving in the direction of the arrow 32 is clamped and brought against the edge 11 of knife 9.

What is claimed is:

1. A method for measuring yarn strength on-line in a processing system comprising the steps of
   exerting a force on an elongated yarn to substantially continuously pass the elongated yarn longitudinally through a spinning or yarn processing machine,
   engaging and holding a section of the yarn with a clamp (1) to resist the force causing the yarn motion and to thereby apply tearing force to the held section of the yarn until the yarn tears, and
   measuring the force required to tear the held section of the yarn as a measure of yarn strength.

2. A method according to claim 1 wherein yarn entering the machine is engaged by the clamp.

3. A method according to claim 1 wherein yarn leaving the machine is engaged by the clamp.

4. A method according to claim 1 in a processing system wherein the force is exerted by a yarn-moving device for substantially continuously moving the yarn through the machine and wherein the engagement of the yarn by the clamp is synchronized to occur at a predetermined position of the yarn-moving device.

5. A method according to claim 1 wherein the machine is a yarn cleaner having electronic measuring means including an optical sensor and a central processing unit for detecting defects in yarn passing therethrough, and wherein the step of measuring the force is carried out using means for force detection and the central processing unit on the machine.

6. A method according to claim 5 and including actuating the clamp with the central processing unit of the electronic measuring means.

7. An apparatus for measuring the strength of a yarn passing substantially continuously and longitudinally through a yarn handling or processing machine comprising the combination of
   means for moving the yarn through the machine;
   a clamp;
   means for selectively actuating said clamp for engaging and holding a portion of the yarn while the yarn is in motion through the machine so that a portion of the yarn held by said clamp resists further yarn motion and the force of the motion causes the yarn to tear;
   means for obtaining test data on the force applied to cause yarn tearing; and
   central processing means for receiving and analyzing said test data and controlling said means for actuating said clamp.

8. An apparatus according to claim 7 and further comprising a yarn cleaner (30) having a sensor (29) for generating signals representative of defects in yarn passing therethrough, means (7) for transmitting signals generated by said sensor (29) to said central processing means (3) for analyzing said signals.

9. An apparatus according to claim 8 wherein said clamp includes cutter means for severing said yarn.

10. An apparatus according to claim 9 wherein said cutter means includes
    a displaceably guided knife (9) having a blade; and
    a drum (13( having an anvil surface; and wherein said means for actuating includes
    drive means (10) for moving said blade of said knife toward said anvil surface of said drum.

11. An apparatus according to claim 10 wherein said clamp, said cutter means and said means or obtaining test data comprise a single mechanical unit.

12. An apparatus according to claim 7 wherein said machine is a cross-wound bobbin winder.

13. An apparatus according to claim 7 wherein said machine is an open-ended spinning machine.

14. An apparatus according to claim 7 wherein said machine is a twisting machine.

* * * * *